US012721934B2

(12) United States Patent
Li et al.

(10) Patent No.: US 12,721,934 B2
(45) Date of Patent: Sep. 1, 2026

(54) CATIONIC NANODRUG, PREPARATION METHOD THEREFOR, AND DRUG-LOADED IMPLANTABLE MEDICAL DEVICE

(71) Applicant: SHANGHAI MICROPORT MEDICAL (GROUP) CO., LTD., Shanghai (CN)

(72) Inventors: Meng Li, Shanghai (CN); Yufu Wang, Shanghai (CN); Junfei Li, Shanghai (CN)

(73) Assignee: SHANGHAI MICROPORT MEDICAL (GROUP) CO., LTD., Shanghai (CN)

( * ) Notice: Subject to any disclaimer, the term of this patent is extended or adjusted under 35 U.S.C. 154(b) by 1218 days.

(21) Appl. No.: 17/640,104

(22) PCT Filed: Sep. 1, 2020

(86) PCT No.: PCT/CN2020/112899

§ 371 (c)(1),
(2) Date: Mar. 3, 2022

(87) PCT Pub. No.: WO2021/043145

PCT Pub. Date: Mar. 11, 2021

(65) Prior Publication Data

US 2022/0288285 A1 Sep. 15, 2022

(30) Foreign Application Priority Data

Sep. 3, 2019 (CN) ......................... 201910828976.0

(51) Int. Cl.

| | |
|---|---|
| ***A61L 31/16*** | (2006.01) |
| ***A61K 9/107*** | (2006.01) |
| ***A61K 9/127*** | (2025.01) |
| ***A61K 9/14*** | (2006.01) |
| ***A61K 9/50*** | (2006.01) |
| ***A61L 31/10*** | (2006.01) |

(52) U.S. Cl.

CPC ............ *A61L 31/16* (2013.01); *A61K 9/1075* (2013.01); *A61K 9/127* (2013.01); *A61K 9/146* (2013.01); *A61K 9/5031* (2013.01); *A61L 31/10* (2013.01); *A61L 2300/416* (2013.01); *A61L 2300/606* (2013.01); *A61L 2400/12* (2013.01)

(58) Field of Classification Search

CPC .... A61L 31/16; A61L 31/10; A61L 2300/416; A61L 2300/606; A61L 2400/12; A61L 2300/802; A61L 31/08; A61L 31/14; A61K 9/1075; A61K 9/127; A61K 9/146; A61K 9/5031; A61K 9/5123; A61K 9/5146; A61K 9/5161; A61K 31/337; A61K 31/436; A61M 31/00

See application file for complete search history.

(56) References Cited

U.S. PATENT DOCUMENTS

| | | | |
|---|---|---|---|
| 2010/0330368 | A1 | 12/2010 | Prud'homme et al. |
| 2013/0122058 | A1 | 5/2013 | Chow et al. |
| 2015/0079155 | A1 | 3/2015 | Jensen et al. |
| 2017/0072033 | A1 | 3/2017 | Dutta et al. |
| 2019/0091162 | A1 | 3/2019 | Cheng |

FOREIGN PATENT DOCUMENTS

| | | | |
|---|---|---|---|
| CN | 101475503 | A | 7/2009 |
| CN | 101775082 | A | 7/2010 |
| CN | 101897975 | A | 12/2010 |
| CN | 102579357 | A | 7/2012 |
| CN | 102861340 | A | 1/2013 |
| CN | 103566374 | A | 2/2014 |
| CN | 107849512 | A | 3/2018 |
| CN | 108137819 | A | 6/2018 |
| CN | 108542894 | A | 9/2018 |
| CN | 110496251 | A | 11/2019 |
| WO | WO-2013174409 | A1 | 11/2013 |
| WO | WO-2018/075822 | A1 | 4/2018 |
| WO | WO-2018135839 | A1 | 7/2018 |
| WO | WO-2018140304 | A1 | 8/2018 |

OTHER PUBLICATIONS

He et al., "Size-controlled lipid nanoparticle production using turbulent mixing to enhance oral DNA dellivery," Acta Biomaterialia, vol. 81 (2018) pp. 195-207, 13 pages.

Wang et al., "Cationic micelle: A promising nanocarrier for gene delivery with high transfection efficiency," J. Gene Med. (2019) 16 pages.

Wang et al., "The review of a new method to prepare nanoparticles rapidly and controllably—Flash nanoprecipitation," Journal of Shihezi University: Natural Science, vol. 34, No. 6 (2016) 7 pages.

Yang et al., "Research progress of nonionic surfactant vesicles in cell drug delivery," Strait Pharmaceutical Journal, vol. 25, No. 10 (2013) 4 pages.

*Primary Examiner* — Quanglong N Truong

(74) *Attorney, Agent, or Firm* — MUNCY, GEISSLER, OLDS & LOWE, P.C.

(57) ABSTRACT

Disclosed are a cationic nanodrug, a preparation method therefor, and a drug-loaded implantable medical device, wherein the cationic nanodrug comprises a vector and a drug loaded on the vector, and the vector comprises one or more of a cationic amphipathic compound and a cationic modifier; the cationic amphipathic compound is a cationic amphipathic compound containing amino and/or acyl; and the cationic modifier is a cationic modifier containing amino and/or acyl. The cationic nanodrug greatly improves the uptake of a drug by cells and has a good slow-release effect.

8 Claims, 3 Drawing Sheets

CATIONIC NANODRUG, PREPARATION METHOD THEREFOR, AND DRUG-LOADED IMPLANTABLE MEDICAL DEVICE

TECHNICAL FIELD

The present disclosure relates to the field of medical devices, and more particularly to a cationic nanodrug, a method of preparing the cationic nanodrug and a drug-loaded implantable medical device.

BACKGROUND

Cardiovascular disease is the world's number one killer, and coronary atherosclerotic heart disease (coronary heart disease) is one of the most mortal diseases that severely threaten our lives and health. At present, percutaneous coronary intervention (PCI) is the major treatment options, and drug-eluting stents (DESs) are the first choice of the PCI. The implanted DES can prevent vascular recoiling and the drug carried by the DES can inhibit the proliferation of vascular smooth muscle cells and prevent the occurrence of endometrial hyperplasia, thus effectively lowering the rate of in-stent restenosis. Recently, drug-coated implantable medical devices, especially drug-coated balloons (DCBs), are attracting increasing interest due to their outstanding advantages such as intervention without implantation, no risk of thrombosis and fast therapeutic response. As an emerging interventional treatment technique, the therapeutic effectiveness and safety of drug-coated implantable medical devices have been verified by numerous clinical trials in treating in-stent restenosis, small blood vessel lesions, bifurcation lesions and the like.

A drug-coated implantable medical device is mainly made by applying a coating containing an antiproliferative drug to the surface of the device. When the drug-coated implantable medical device is delivered to a lesion location, the drug will be released from the drug coating within a very short time (30-60 s) during expansion to inhibit the proliferation of vascular smooth muscle cells. Therefore, the design of the drug coating on the implantable medical device is of great significance.

For the drug coating on implantable medical device, the current designs concentrate on the reduction of loss during delivery and enhancement of drug uptake by the target lesion. So far, drug coatings with various hydrophilic substrates have been designed and manufactured. Typically, such drug coatings further have a hydrophilic top layer that can slow dissolution to significantly reduce loss of the drug coating during delivery. However, these drug coatings suffer from poor uptake and retention and are not capable of the sustained release. How to improve the drug uptake and retention and thus enhance the sustained release of drug coatings has also been an important factor that hinders the development of implantable medical devices.

SUMMARY

Therefore, there is a need to provide a cationic nanodrug, preparation method therefor and a drug-loaded implantable medical device, which can provide a good sustained release.

The present disclosure provides a cationic nanodrug comprising a carrier and a drug carried by the carrier. The carrier comprises one or more of a cationic amphiphilic compound and a cationic modifier. The cationic amphiphilic compound is an amino and/or acyl-containing cationic amphiphilic compound, and the cationic modifier is an amino and/or acyl-containing cationic modifier.

In one embodiment, the carrier further comprises a hydrophobic nanocore, and either or both of the cationic amphiphilic compound and the cationic modifier comprise hydrophilic terminals and hydrophobic terminals. The hydrophobic terminal is bonded to the hydrophobic nanocore, and the hydrophilic terminal is at least partially exposed.

In one embodiment, the cationic modifier is selected from one or more of the group consisting of cationic phospholipids, polyamino acids, polysaccharides, polypeptides, cholesterol derivatives and cationic copolymers.

In one embodiment, the cationic modifier is selected from one or more of the group consisting of polyarginine polylysine, diethylaminoethyl-dextran, hydroxypropyltrimethyl ammonium chloride chitosan, chitosan hydrochloride, N,N,N-trimethyl chitosan, TAT polypeptide, and 3β-[N—(N',N'-dimethylaminoethyl)-carbamoyl]cholesterol.

In one embodiment, the cationic amphiphilic compound is a cationic surfactant selected from one or more of the group consisting of 1,2-dioleoyl-3-trimethylammonium-propane chloride, 1,2-dioleoyl-sn-glycero-3-phosphoethanolamine, 1,2-distearoyl-3-trimethylammonium-propane, 1,2-dimyristoyl-3-trimethylammonium-propane mesylate, 1,2-dipalmitoyl-3-trimethylammonium-propane, 1,2-distearoyl-3-trimethylammonium-propane, poly(N,N-dimethylaminoethyl methacrylate)-based amphiphilic polymers, chitosan-based amphiphilic polymers, chitosan quaternary ammonium salt based amphiphilic polymers, chitosan chloride-based amphiphilic polymers, sulfhydryl-modified chitosan-based amphiphilic polymers, and polyethyleneimine-based amphiphilic polymers and poly(β-amino esters) based amphiphilic polymers.

In one embodiment, the carrier further comprises an emulsifier when the carrier comprises the cationic modifier.

In one embodiment, the emulsifier is selected from one or more of the group consisting of D-α-tocopherol polyethylene glycol succinate, polyvinyl alcohol, polysorbate, poloxamer and carbomer.

In one embodiment, the carrier further comprises a sustained release copolymer.

In one embodiment, the cationic nanodrug has a surface charge of 10-60 mV, and/or the cationic nanodrug has a particle size of 3-300 nm.

In one embodiment, the cationic nanodrug has a morphology of sphere, rod, worm or disc.

In one embodiment, the drug carried by the carrier is an antiproliferative drug selected from one or more of the group consisting of paclitaxel, sirolimus and derivatives of sirolimus. The derivatives of sirolimus may be zotarolimus, everolimus, biolimus, 7-O-demethyl rapamycin, temsirolimus, rdaforolimus and tacrolimus. The antiproliferative drug may be in a form of the crystalline, amorphism, or combination thereof.

The present disclosure also provides a medical device comprising a substrate and a drug coating on the substrate. The drug coating contains the cationic nanodrug as described above.

The present disclosure also provides a method of preparing a cationic nanodrug, comprising the steps of:

providing a first liquid stream;

providing a second liquid stream; and performing an instantaneous nanoprecipitation process in which the first and second liquid streams collide with each other to create a vortex stream where the two streams are mixed to form a nanosuspension, and obtaining the cationic nanodrug through collecting and dialyzing the nanosuspension, wherein a drug is dissolved in at least one of the first and second liquid streams and a carrier is dissolved in at least one of the first and second liquid streams, wherein one of the first and second liquid streams contains a water-soluble organic phase, and the other one of the first and second liquid streams contains an aqueous phase, wherein the carrier comprises one or more of a cationic amphiphilic compound and a cationic modifier, the cationic amphiphilic compound being an amino- and/or acyl-containing cationic amphiphilic compound, the cationic modifier being an amino- and/or acyl-containing cationic modifier.

In one embodiment, the cationic modifier is selected from the group consisting of cationic phospholipids, polyamino acids, polysaccharides, polypeptides, cholesterol derivatives and cationic copolymers.

In one embodiment, the cationic modifier is selected from one or more of the group consisting of polyarginine, polylysine, diethylaminoethyl-dextran, hydroxypropyltrimethyl ammonium chloride chitosan, chitosan hydrochloride, N,N,N-trimethyl chitosan, TAT polypeptide, and 3β-[N—(N',N'-dimethylaminoethyl)-carbamoyl]cholesterol.

In one embodiment, the cationic amphiphilic compound is a cationic surfactant selected from one or more of the group consisting of 1,2-dioleoyl-3-trimethylammonium-propane chloride, 1,2-dioleoyl-sn-glycero-3-phosphoethanolamine, 1,2-distearoyl-3-trimethylammonium-propane, 1,2-dimyristoyl-3-trimethylammonium-propane mesylate, 1,2-dipalmitoyl-3-trimethylammonium-propane, 1,2-distearoyl-3-trimethylammonium-propane, poly(N,N-dimethylaminoethyl methacrylate)-based amphiphilic polymers, chitosan-based amphiphilic polymers, chitosan quaternary ammonium salt based amphiphilic polymers, chitosan chloride-based amphiphilic polymers, sulfhydryl-modified chitosan-based amphiphilic polymers, and polyethyleneimine-based amphiphilic polymers and poly(β-amino esters) based amphiphilic polymers.

In one embodiment, a sustained release copolymer is dissolved in at least one of the first and second liquid streams, and/or an emulsifier is dissolved in at least one of the first and second liquid streams.

In one embodiment, the sustained release copolymer is poly(lactic-co-glycolic acid), and/or the emulsifier is selected from one or more of the group consisting of D-α-tocopherol polyethylene glycol succinate, polyvinyl alcohol, polysorbate, poloxamer and carbomer.

In one embodiment, performing the instantaneous nanoprecipitation process in which the first and second liquid streams collide with each other to create the vortex stream may comprise the steps of:

providing a vortex mixer;

introducing the first liquid stream into one channel of the vortex mixer;

introducing the second liquid stream to another channel of the vortex mixer; and colliding and mixing the first liquid stream with the second liquid stream in the vortex mixer to form the vortex stream.

In one embodiment, performing the instantaneous nanoprecipitation process in which the first and second liquid streams collide with each other to create the vortex stream further comprises introducing water into remaining channel(s) of the vortex mixer as additional liquid stream(s); and colliding and mixing the first liquid stream, the second liquid stream and the additional liquid stream(s) in the vortex mixer to form the vortex stream.

In one embodiment, the additional liquid stream(s) may include a third liquid stream and a fourth liquid stream.

In one embodiment, the third and the fourth liquid streams may have a same flow rate. In one embodiment, the first, second and third liquid streams each have a flow rate ranging from 1 mL/min to 12 mL/min, and a ratio of the flow rate of the first liquid stream to the flow rate of the second liquid stream is 1:1. The or each additional liquid stream in the remaining channel(s) is introduced at a flow rate that is 1 to 5 times that of the first or second liquid stream.

The present disclosure also provides a drug-loaded implantable medical device comprising a cationic nanodrug prepared by the method as described above.

Since the used cationic amphiphilic compound and/or cationic modifier cause(s) the surface of the cationic nanodrug to have positive charges, the cationic nanodrug is able to effectively and fully bond vascular wall cells having negative charges, thereby allowing to greatly enhance the uptake of the nanodrug particles by tissue cells. In particular, the amino or acyl group contained in the above amphiphilic compound and/or cationic modifier enables to help the nanodrug particles in escaping from cellular lysosomes through the "proton pump action", thereby allowing to avoid the degradation or extracellular transportation of drugs by lysosomes. Therefore, the above cationic nanodrug has excellent tissue retention time to offer a good sustained release property, which facilitates a long-term inhibitory effect against the proliferation of vascular smooth muscle cells. Further, the cationic nanodrug has a good biocompatibility, thereby enabling to avoid the introduction of the additional cytotoxicity.

Moreover, as the cationic nanodrug is in the nanoscale, it has an increased drug loading capacity and is able to effectively avoid the problem of embolization that may be caused by large particles dropping from conventional drug coatings, resulting in a significant increase in safety. Further, under the action of the amino or acyl-containing cationic amphiphilic compound and/or cationic modifier, the above cationic nanodrug particle enables to increase the affinity between the carrier and the drug, which in turn greatly increase the drug loading capacity of the cationic nanodrug particle. In other words, for the same drug concentration, the above cationic nanodrug particle allows to reduced use of excipients and coating thickness. The reduced coating thickness results in improved crossability of a drug-loaded implantable medical device.

Besides, the use of instantaneous nanoprecipitation process enables to rapidly prepare the cationic nanodrug particle having an extremely high drug loading capacity. Compared to conventional preparation method of nanoparticles, the instantaneous nanoprecipitation has a wide range of advantages including simple operation, an extremely short process time (several seconds), a high drug loading capacity and adjustable particle size of the resulting nanoparticles and linear scalability to a larger industrial scale.

Furthermore, the use of the instantaneous nanoprecipitation process allows nanoparticles of the cationic nanodrug to have a particle size of about 200 nm. Compared to the drug particle having a particle size of the micron or even millimeter order prepared by a conventional method, the cationic nanodrug prepared by the instantaneous nanoprecipitation enables to strengthen the permeation of nanoparticles to enhance the drug uptake of tissues. Moreover, as the addition of the cationic amphiphilic compound and/or cationic modifier causes the surface of the cationic nanodrug particles to have positive charges, the cationic nanodrug is able to effectively and fully bond vascular wall cells having negative charges, thereby allowing to greatly enhance the uptake of the nanodrug particles by tissue cells. In addition, the surface potential of the cationic nanodrug can be adjusted by changing the content of the cationic surfactant. This in turn contributes to facilitate bonding of the cationic nanodrug to vascular wall cells and to regulate retention time of the cationic nanodrug in tissue to achieve a desirable sustained release effect.

DETAILED DESCRIPTION

Figure 1:
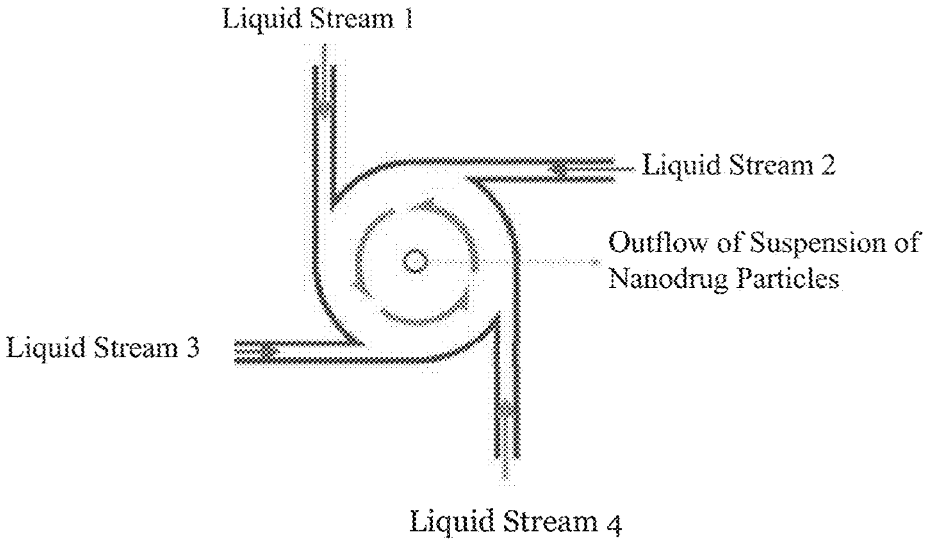
FIG. 1 is a schematic diagram of a vortex mixer according to an embodiment.

In order to facilitate understanding of present disclosure, the present disclosure is described more fully and preferred embodiments thereof are given below. However, the present disclosure may be implemented in many different forms and should not be limited by the embodiments set forth herein. Rather, these embodiments are provided for the purpose that this disclosure will be thoroughly and completely understood.

Unless otherwise defined, all technical and scientific terms used herein have the same meaning as commonly understood by the skilled in the art to which this disclosure belongs. The terminology used herein is for the purpose of describing particular embodiments only and is not intended to limit the present disclosure. As used herein, the term "and/or" includes any and all combinations of one or more of the associated listed items.

The present disclosure provides a cationic nanodrug comprising a carrier and a drug carried by the carrier. The carrier includes one or more of a cationic amphiphilic compound and a cationic modifier. The cationic amphiphilic compound is an amino and/or acyl-containing cationic amphiphilic compound. The cationic modifier is an amino and/or acyl-containing cationic modifier.

The amino or acyl-containing cationic amphiphilic compound and/or cationic modifier used in present disclosure is able to help the nanodrug particles in escaping from cellular lysosomes through the "proton pump action", thereby allowing to avoid the degradation or extracellular transportation of drugs by lysosomes. Therefore, the cationic nanodrug of present disclosure has an excellent tissue retention time, which facilitates a long-term inhibitory effect against the proliferation of vascular smooth muscle cells. Moreover, the cationic nanodrug of present disclosure has a good biocompatibility, thereby enabling to avoid the introduction of the additional cytotoxicity.

The carrier in the cationic nanodrug further includes a hydrophobic nanocore, and the cationic amphiphilic compound and the cationic modifier each include a hydrophilic terminal and a hydrophobic terminal. The hydrophobic terminal is absorbed on the hydrophobic nanocore, while the hydrophilic terminal is at least partially exposed. The absorption of the hydrophobic terminal on the hydrophobic nanocore enables to prevent growth of the nanoparticle, and the at least partially exposed hydrophilic terminal can not only protect the particle externally but also prevent mutual aggregation of nanoparticles, thus facilitating the formation of nanoparticles having a small and uniform particle size. It will be appreciated that, here, the "the exposed hydrophilic terminal" means that the hydrophilic terminal is exposed outside the hydrophobic nanocore relative to the hydrophobic terminal in the center, i.e., relative to the hydrophobic terminal. The case in which the nanoparticles interact with each other or with other molecules (e.g., solvent molecules) to envelop the hydrophilic terminal is contemplated within the scope of the present disclosure.

It will be appreciated that the various agents used in present disclosure (e.g., the cationic amphiphilic compound, the cationic modifier, etc.) are all pharmaceutically acceptable. According to present disclosure, the hydrophobic nanocores may be formed by any suitable substance acceptable in the art, such as a supersaturated organic solute. This is not limited herein.

In present disclosure, each of the cationic amphiphilic compound and cationic modifier contains an amino or acyl group. That is, the cationic amphiphilic compound and cationic modifier is required to contain only one amino or acyl group. It will be appreciated that agents containing only amino group(s), only acyl group(s) or both amino and acyl groups are also contemplated within the scope of the present disclosure.

Further, the cationic modifier is selected from one or more of the group consisting of cationic phospholipids, cationic copolymers, polyamino acids, polysaccharides, polypeptides and cholesterol derivatives. Preferably, the cationic modifier is a biodegradable copolymer that would not result in the accumulation of toxic substances after degradation. The polyamino acids, the polysaccharides, the polypeptides or the cholesterol derivatives are all biological analogs that naturally occur in the human body and their degradation has no toxic side effect, thereby having a high application value.

Furthermore, the cationic modifier is selected from one or more of the group consisting of polyarginine, polylysine, diethylaminoethyl-dextran, hydroxypropyltrimethyl ammonium chloride chitosan, chitosan hydrochloride, N,N,N-trimethyl chitosan, TAT polypeptide, and 3β-[N—(N',N'-dimethylaminoethyl)-carbamoyl]cholesterol.

Furthermore, the cationic amphiphilic compound is an cationic surfactant selected from one or more of the group consisting of: 1,2-dioleoyl-3-trimethylammonium-propane (DOTAP) chloride, 1,2-dioleoyl-sn-glycero-3-phosphoethanolamine (DOPE), 1,2-distearoyl-3-trimethylammonium-propane (DSTAP), 1,2-dimyristoyl-3-trimethylammonium-propane (DMTAP) mesylate, 1,2-dipalmitoyl-3-trimethylammonium-propane (DPTAP), 1,2-distearoyl-3-trimethylammonium-propane (DSTAP), poly(N,N-dimethyl amino ethyl methacrylate)-based amphiphilic polymers, chitosan-based amphiphilic polymers, amphiphilic polymers based on quaternary ammonium salts of chitosan, chitosan chloride-based amphiphilic polymers, sulfhydryl-modified chitosan-based amphiphilic polymers, polyethyleneimine-based amphiphilic polymers and poly(β-amino esters) based amphiphilic polymers.

The above cationic surfactants and cationic modifiers are of good biocompatibilities and are safe as they are not likely to result in a toxic side effect. The above cationic surfactants and cationic modifiers have greatly improved safety over the agents of didodecyldimethylammonium bromide (DMAB) and the like. Moreover, the surface potential of the cationic nanodrug can be adjusted by changing the concentration(s) of the cationic amphiphilic compound and/or the cationic modifier. This in turn contributes to facilitate bonding of the cationic nanodrug to vascular wall cells and to regulate retention time of the cationic nanodrug in tissue to achieve a desirable sustained release effect.

Further, in the case that the carrier is the cationic modifier, it may further include an emulsifier. It will be appreciated that the present disclosure is not limited to any particular method of loading the emulsifier in the cationic nanodrug. It may be absorbed onto the nanocore via absorption, or otherwise loaded in the cationic nanodrug via its interaction with the cationic amphiphilic compound and/or the cationic modifier. It should be understood that the loading methods of the emulsifier vary depending on the selected agents and preparation method, which are all contemplated within the scope of the present disclosure.

Furthermore, the emulsifier is selected from one or more of the group consisting of D-α-tocopherol polyethylene glycol succinate, polyvinyl alcohol, polysorbate, poloxamer and carbomer. These agents have no toxic side effect and can improve safety of the prepared cationic nanodrug.

In addition, the above carrier further includes a sustained release copolymer. The sustained release copolymer refers to a polymer capable of slowing release of the drug from the nanoparticles when loaded in the cationic nanodrug. It will be appreciated that the present disclosure is not limited to any particular method of loading the sustained release copolymer in the cationic nanodrug. The sustained release copolymer may be absorbed onto the nanocore via the absorption, or otherwise loaded in the cationic nanodrug via its interaction with the cationic amphiphilic compound and/or the cationic modifier. It should be understood that the loading methods of the sustained release copolymer vary depending on the selected agents and preparation method, which are all contemplated within the scope of the present disclosure. For example, when PLGA is used as the sustained release copolymer, it may be encapsulated within the cationic nanodrug due to its hydrophobic property.

The addition of the sustained release copolymer can enhance the sustained release property. It will be appreciated that the sustained release copolymer in present disclosure may be any pharmaceutically acceptable biodegradable copolymer, which is not limited herein. The sustained release copolymer is preferred to be a polymer that can be degraded into non-toxic substances in human body. In one embodiment, the copolymer is poly(lactic-co-glycolic acid) (PLGA) that can be degraded in the body into lactic acid and glycolic acid, each of which is the by-product in human metabolic pathways without a toxic side effect.

By using the cationic amphiphilic compound and/or the cationic modifier as the carrier in present disclosure, it enables the surface of the cationic nanodrug to have positive charges. The surface of the cationic nanodrug has a charge potential (i.e., $\zeta$) of preferably 1-80 mV, more preferably 10-60 mV, e.g., 20-50 mV.

It will be appreciated that the cationic nanodrug of the present disclosure is a nanoscale (1-1000 nm) drug. The particle size of the cationic nanodrug is preferably of 3-300 nm, more preferably of 50-250 nm, such as 70-240 nm, 80-230 nm and 100-210 nm. The nanodrug has a variety of advantages including enhanced cellular penetration, increased drug loading, sustained release, local retention and prevention of drug degradation. Therefore, when applying a coating containing the above cationic nanodrug to an implantable medical device, the problem of embolization that may be caused by large particles dropping from conventional drug coatings can be circumvented, resulting in a significant increase in safety.

The present disclosure is not limited to any particular morphology of the cationic nanodrug. The preferred morphology is sphere, rod, worm and disc. The more preferred morphology is sphere due to an improved drug loading. Depending on the specific process used, the cationic nanodrug may be implemented as one of cationic micelles, cationic polymer nanoparticles, cationic liposome, and mixtures thereof.

The present disclosure is not limited to any particular method of loading the drug in the carrier, and the loading method may vary depending on the preparation process and agents used. For example, the drug may be encapsulated in the carrier or loaded on the surface of the carrier, which is interpreted within the scope of present disclosure. Moreover, the present disclosure is not limited to any particular type of the drug, and it may be chosen as needed. In one embodiment, the drug is an antiproliferative drug, such as paclitaxel, sirolimus or a derivative of sirolimus. The derivative of sirolimus is preferably zotarolimus, everolimus, biolimus, 7-O-demethyl rapamycin, temsirolimus, rdaforolimus or tacrolimus. The antiproliferative drug may be in a form of the crystalline, amorphism, or combination thereof.

The cationic nanodrug of the present disclosure is a nanoscale drug with a large relative surface area, which allows a significantly increased drug loading. Moreover, the amino or acyl-containing cationic amphiphilic compound and/or cationic modifier is/are used as the carrier in preparation of the cationic nanodrug of the present disclosure, which enables to strengthen affinity between the carrier and the drug, thereby further improving the drug loading. Besides, drug loading control can be conveniently and quickly accomplished by adjusting the concentration ratios of various agents and the particle size of the prepared cationic nanodrug. In one embodiment, the drug loading of the above cationic nanodrug is 1-50% (w/w), for example, 10-50% or 20-50%.

The present disclosure is not limited to any particular preparation method of the cationic nanodrug, while the use of instantaneous nanoprecipitation is preferred. This method is simple, fast, scalable and capable of fast and continuously preparing nanoparticles with a narrow particle size distribution and a large drug loading capacity.

The present disclosure also provides a method of preparing the cationic nanodrug, comprising the steps as follows:

S101: Providing a first liquid stream and a second liquid stream. The drug is dissolved in at least one of the first and second liquid streams. The carrier is dissolved in at least one of the first and second liquid streams. One of the first and second liquid streams contains a water-soluble organic phase, and the other contains an aqueous phase. The carrier comprises one or more of a cationic amphiphilic compound and a cationic modifier. The cationic amphiphilic compound is an amino- and/or acyl-containing cationic amphiphilic compound. The cationic modifier is an amino- and/or acyl-containing cationic modifier.

In step S101, the organic phase is not limited to any particular substance. Examples thereof may include, but are not limited to, acetone and alcohol based solvents.

Further, the cationic modifier is selected from one or more of the group consisting of cationic phospholipids, cationic copolymers, polyamino acids, polysaccharides, polypeptides and cholesterol derivatives. Preferably, the cationic modifier is a biodegradable copolymer that would not result in the accumulation of toxic substances after degradation.

The polyamino acids, the polysaccharides, the polypeptides or the cholesterol derivatives are all biological analogs that naturally occur in the human body and their degradation has no toxic side effect, thereby having a high application value.

Furthermore, the cationic modifier is selected from one or more of the group consisting of polyarginine, polylysine, diethylaminoethyl-dextran, hydroxypropyltrimethyl ammonium chloride chitosan, chitosan hydrochloride, N,N,N-trimethyl chitosan, TAT polypeptide, and 3β-[N—(N',N'-dimethylaminoethyl)-carbamoyl]cholesterol.

The cationic amphiphilic compound is an cationic surfactant selected from one or more of the group consisting of: 1,2-dioleoyl-3-trimethylammonium-propane (DOTAP) chloride, 1,2-dioleoyl-sn-glycero-3-phosphoethanolamine (DOPE), 1,2-distearoyl-3-trimethylammonium-propane (DSTAP), 1,2-dimyristoyl-3-trimethylammonium-propane (DMTAP) mesylate, 1,2-dipalmitoyl-3-trimethylammonium-propane (DPTAP), 1,2-distearoyl-3-trimethylammonium-propane (DSTAP), poly(N,N-dimethylaminoethyl methacrylate)-based amphiphilic polymers, chitosan-based amphiphilic polymers, amphiphilic polymers based on quaternary ammonium salts of chitosan, chitosan chloride-based amphiphilic polymers, thiol-modified chitosan-based amphiphilic polymers, polyethyleneimine-based amphiphilic polymers and amphiphilic polymers based on poly(β-amino esters). Further, the sustained release copolymer is dissolved in at least one of the first and second liquid streams. The sustained release copolymer may be poly (lactic-co-glycolic acid).

Further, the emulsifier is dissolved in at least one of the first and second liquid streams. The emulsifier may be selected from one or more of the group consisting of D-α-tocopherol polyethylene glycol succinate, polyvinyl alcohol, polysorbate, poloxamer and carbomer.

It will be appreciated that, for each of the above agents, it may be dissolved either in the organic phase or in the aqueous phase depending on the type of the specific agent, and present disclosure is not particularly limited in this regard. For example, most existing drugs and cationic surfactants are easily soluble in organic solvent, sustained release copolymers being easily soluble in organic phases, the cationic modifiers being easily soluble in water. Therefore, both the cationic surfactant and the sustained release copolymer may be added to the organic phase, while the cationic modifier may be added to the aqueous phase.

Additionally, in order to facilitate the preparation of the cationic nanodrug, the emulsifier, for example, selected from one or more of D-α-tocopherol polyethylene glycol succinate (TPGS), polyvinyl alcohol, polysorbate, poloxamer and carbomer may be added to the first liquid stream and/or the second liquid stream. Preferably, the emulsifier is added to the second liquid stream, and is optionally added to the first liquid stream depending on the type of the specific agent.

The various agents may be added at a ratio that is adjustable as needed, and the present disclosure is not limited in this regard. In particular, by adjusting contents of the cationic amphiphilic compound and the cationic modifier, it enables to achieve adjustments of the surface potential of the cationic nanodrug, which is important to the drug's affinity with cells.

The drug loaded is not limited to any particular type and may be chosen as needed. In one embodiment, the drug is an antiproliferative drug such as paclitaxel, sirolimus or a derivative of sirolimus. In particular, the derivative of sirolimus may be zotarolimus, everolimus, biolimus, 7-O-demethyl rapamycin, temsirolimus, rdaforolimus or tacrolimus. The antiproliferative drug is in a form of crystalline, amorphism, or combination thereof.

S102: Performing an instantaneous nanoprecipitation process in which the first and second liquid streams collide with each other to create a vortex stream where the two streams are mixed to form a nanosuspension, and obtaining the cationic nanodrug through collecting and dialyzing the nanosuspension.

The instantaneous nanoprecipitation is a method using a multi-channel vortex mixer to cause several liquid streams to collide at high speeds, achieving a sufficiently high degree of supersaturation of organic solutes therein within a very short time (several seconds or even milliseconds), which results in the formation of hydrophobic nanocores. According to present disclosure, the hydrophobic terminals of the cationic amphiphilic compound and/or cationic modifier are absorbed onto the hydrophobic nanocores to avoid the further growth of the nanocore, while the hydrophilic terminals of the cationic amphiphilic compound and/or cationic modifier are exposed outside the nanoparticles to prevent the aggregation of the nanocore. Therefore, uniformly sized nanoparticles can be obtained.

It should be noted that the multi-channel vortex mixer may have a varying number of channels depending on the type of the selected mixer, and the present disclosure is not limited in this regard. In present disclosure, any suitable multi-channel vortex mixer having two or more channels may be chosen. For example, a four-channel vortex mixer as shown in FIG. 1 may be used, which has a first channel for introducing the first liquid stream, a second channel for introducing the second liquid stream, and third and fourth channels both for introducing water as third and fourth liquid streams, respectively.

Flow rates of liquid streams in respective channels may be determined as appropriate and are preferred to ranges from 1 mL/min to 12 mL/min such as, for example, from 2 mL/min to 11 mL/min, from 3 mL/min to 10 mL/min, from 5 mL/min to 9 mL/min or from 6 mL/min to 8 mL/min. The flow rates of liquid streams in respective channels may be equal or not. Preferably, the flow rates of the third and fourth liquid streams are equal to each other. Preferably, a flow rate ratio of the first liquid stream to the second liquid stream is 1:1, and the flow rates of the third and fourth liquid streams each are 1 to 5 times, such as 1 to 4 times, more preferably, 1 to 3 times that of the first or second liquid stream. This enables the formation of the cationic nanodrug having a uniform small particle size.

Besides, the dialysis may be accomplished by any commonly used method in the art, and present disclosure is not limited to any particular method. For example, the suspension to be dialyze may be placed in a dialysis bag for dialysis, and the water may be exchanged at regular intervals. Subsequently, the resulting suspension of the nanodrug particles may be concentrated for subsequent use.

The present disclosure also provides a drug-loaded implantable device including a substrate and a drug coating on the substrate. The drug coating contains the above cationic nanodrug that may be prepared using the above method.

As the drug-loaded implantable device includes the above cationic nanodrug that is prepared using the above method, it has a good biocompatibility. Moreover, since particles of the cationic nanodrug have an adjustable surface potential, when implanted, the cationic nanodrug loaded implantable device allows to significantly enhance the uptake of the drug by a target lesion by virtue of the electrostatic interaction and the high permeability of the cationic nanodrug particles.

Additionally, since the drug encapsulated within the cationic nanoparticles can be released in a sustained manner, the cationic nanodrug loaded implantable device can provide a long-term inhibitory effect against the proliferation of vascular smooth muscle cells.

It will be appreciated that the drug coating may be obtained by spraying or otherwise. Once a required drug concentration in the drug coating is reached, the drug coating may be dried and sterilized.

The drug-loaded implantable device of present disclosure can be used either in vitro or in vitro for either short- or long-term implantation. Moreover, the medical device may be the medical device used in the treatment or diagnosis of arrhythmias, heart failures, valvular disease, vascular disease, diabetes, neurological diseases and disorders, as well as in orthopedic, neurological, oncological, ophthalmological and ENT surgery. Examples of the medical device of the present disclosure may include, but are not limited to, stents, stent grafts, anastomotic connectors, synthetic patches, leads, electrodes, needles, guide wires, catheters, sensors, surgical instruments, angioplasty balloons, wound drains, shunts, tubing, infusion sleeves, intraurethral cannula, pellets, implants, blood oxygenators, pumps, vascular grafts, vascular access ports, heart valves, annuloplasty rings, sutures, surgical clips, surgical staples, pacemakers, implantable defibrillators, neurostimulators, orthopedic devices, cerebrospinal fluid shunts, implantable drug pumps, spinal cages, artificial discs, replacement devices for nucleus pulposus, ear tubes, intraocular lens and tubing used in minimally invasive surgeries. The stents may include, but are not limited to, coronary arterial stents, peripheral vascular stent, intracranial vascular stents, urethral stents and esophageal stents, with coronary arterial stents being preferred.

In one embodiment, the substrate is a balloon, and the drug-loaded implantable device is a drug-coated balloon.

The cationic nanodrug loaded implantable device of the present disclosure allows to significantly enhance uptake of the drug by a target lesion by virtue of both electrostatic interaction and the high permeability of the nanoparticles. Moreover, the cationic nanodrug can help the nanoparticles escape to cytoplasm under the action of "proton pumping", allowing to avoid the degradation or extracellular transportation of drugs by lysosomes. Since the drug in the nanoparticles that escape to cytoplasm is encapsulated by a polymer, it can be released in a sustained manner, allowing the drug to be retained in tissue for a significantly prolonged time and enabling the drug-loaded implantable device with the cationic nanodrug coating to provide a long-term inhibitory effect against the proliferation of vascular smooth muscle cells. Additionally, the nanoscale drug particles are able to prevent distal embolization, thereby great increasing safety. Compared to conventional nanoparticle drugs, the nanoparticle drug of the present disclosure possesses an extremely high drug loading capacity, allowing to cut down the use of excipients and surfactants, and reduce thickness of the coating on the drug balloon, which thus improve the crossability of the drug-loaded balloon. Furthermore, the preparation method of the cationic nanodrug is simple, time-saving, capable of adjusting particle size, and enables to offer a high drug loading capacity. Moreover, such method can be scaled up easily, thereby having a wide future application in the industry.

Specific examples are set forth below to further illustrate the present disclosure.

Example 1

Sirolimus, D-α-tocopherol polyethylene glycol succinate (TPGS) and poly(lactic-co-glycolic acid) (PLGA) were completely dissolved in acetone to form a solution serving as the liquid stream 1 and having concentrations of 10 mg/mL of Sirolimus, 2 mg/mL of TPGS and 5 mg/mL of PLGA. TPGS and hydroxypropyltrimethyl ammonium chloride chitosan (HACC) was dissolved in water to form the solution serving as the liquid stream 2 and having concentrations of 0.3 mg/mL of TPGS and 0.08 mg/mL of HACC. Water was served as both the liquid stream 3 and liquid stream 4. These liquids were then introduced by an injection pump to a four-channel vortex mixer as four liquid streams (i.e., said liquid streams 1, 2, 3 and 4) at a flow rate of 10 mL/min, where they were mixed to form a suspension of nanodrug particles. The mixing might last for an appropriate period of time depending on a desired volume of the suspension of cationic nanodrug particles. In this example, the mixing lasted for 10 seconds, and the resulting suspension of nanodrug particles had an aqueous phase and an organic phase in a volume ratio of 1:3. In order to achieve a homogeneous suspension, the mixture formed in the first 2 seconds was discarded and the mixture formed in the subsequent 8 seconds was collected as the suspension of cationic nanodrug particles. The collected suspension of nanodrug particles was dialyzed for 12 hours in a dialysis bag and the water was exchanged for fresh water at 2-hour intervals. The so-processed suspension of cationic nanodrug particles was then concentrated for subsequent use. Particle size and surface potential of the nanodrug particles were measured and characterized using a Malvern ZS90 instrument. The high-performance liquid chromatography (HPLC) system was used to measure a drug loading of the nanodrug particles, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 $mg/mm^2$. Then, the balloon was naturally dried for 24 hours and sterilization by epoxyethane. In this way, a drug-coated balloon of Example 1 was obtained.

Example 2

1,2-dioleoyl-sn-glycero-3-phosphoethanolamine (DOPE), DC-cholesterol, DOTAP and sirolimus were dissolved in ethanol to form a solution serving as the liquid stream 1 and having concentrations of 3 mg/mL of DOPE, 1 mg/mL of DC-cholesterol, 1 mg/mL of DOTAP and 8 mg/mL of sirolimus. Water was served as each of the liquid streams 2, 3, 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic drug-loaded liposomes. The liquid streams 1 and 2 were both introduced at a flow rate of 10 mL/min, while the liquid streams 3 and 4 were both introduced at a flow rate of 45 mL/min. The resulting suspension of cationic drug-loaded liposomes had an aqueous phase and an organic phase in a volume ratio (v:v) of 1:10. The mixing might last for an appropriate period of time depending on a desired volume of the suspension of cationic drug-loaded liposomes. In this example, the mixing lasted for 10 seconds. In order to achieve a homogeneous suspension of cationic drug-loaded liposomes, the mixture formed in the first 2 seconds was discarded and the mixture formed in the subsequent 8 seconds was collected as the suspension of cationic drug-loaded liposomes. The collected suspension of cationic drug-loaded liposomes was dialyzed for 10 hours in a dialysis bag and the water was exchanged for fresh water at 2-hour intervals. Particle size and surface potential of the cationic drug-loaded liposomes were measured and characterized using a Malvern ZS90 instrument. The high-performance liquid chromatography (HPLC) system was used to measure a drug loading of the cationic drug-loaded liposomes, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 2 was obtained.

Example 3

1,2-dioleoyl-3-trimethylammonium-propane chloride (DOTAP), DC-cholesterol and sirolimus were dissolved in ethanol to form a solution serving as the liquid stream 1 and having concentrations of 3 mg/mL of DOTAP, 1 mg/mL of DC-cholesterol, 8 mg/mL of sirolimus. Water was served as each of the liquid streams 2, 3, 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic drug-loaded liposomes. The mixing might last for an appropriate period of time depending on a desired volume of the suspension of cationic drug-loaded liposomes. In this example, the mixing lasted for 10 seconds. The resulting suspension of cationic drug-loaded liposomes had an aqueous phase and an organic phase in a volume ratio of 1:3. In order to achieve a homogeneous suspension of cationic drug-loaded liposomes, the mixture formed in the first 2 seconds was discarded and the mixture formed in the subsequent 8 seconds was collected as the suspension of cationic drug-loaded liposomes. The collected suspension of cationic drug-loaded liposomes was dialyzed for 10 hours in a dialysis bag and the water was exchanged for fresh water at 2-hour intervals. Particle size and surface potential of the cationic drug-loaded liposomes were measured and characterized using a Malvern ZS90 instrument. The high-performance liquid chromatography (HPLC) system was used to measure a drug loading of the cationic drug-loaded liposomes, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 3 was obtained.

Example 4

1,2-dimyristoyl-3-trimethylammonium-propane (DMTAP) mesylate, DC-cholesterol and sirolimus were dissolved in ethanol to form a solution serving as the liquid stream 1 and having concentrations of 3 mg/mL of DMTAP, 1 mg/mL of DC-cholesterol and 8 mg/mL of sirolimus. A solution of polyvinyl alcohol in water at a concentration of 0.4 mg/mL was served as the liquid stream 2. Water was served as the liquid streams 3, 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic drug-loaded liposomes. The mixing might last for an appropriate period of time depending on a desired volume of the suspension of cationic drug-loaded liposomes. In this example, the mixing lasted for 10 seconds. The resulting suspension of cationic drug-loaded liposomes had an aqueous phase and an organic phase in a volume ratio (v:v) of 1:3. In order to achieve a homogeneous suspension of cationic drug-loaded liposomes, the mixture formed in the first 2 seconds was discarded and the mixture formed in the subsequent 8 seconds was collected as the suspension of cationic drug-loaded liposomes. The collected suspension of cationic drug-loaded liposomes was dialyzed for 10 hours in a dialysis bag and the water was exchanged for fresh water at 2-hour intervals. Particle size and surface potential of the cationic drug-loaded liposomes were measured and characterized using a Malvern ZS90 instrument. The high-performance liquid chromatography (HPLC) system was used to measure a drug loading of the cationic drug-loaded liposomes, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 4 was obtained.

Example 5

N-[1-(2,3-dioleyloxy) propyl]-N,N-dimethylamine (DODMA), DC-cholesterol, DOTAP and sirolimus were dissolved in ethanol to form a solution serving as the liquid stream 1 and having concentrations of 3 mg/mL of DODMA, 1 mg/mL of DC-cholesterol, 1 mg/mL of DOTAP and 8 mg/mL of sirolimus. A solution of tween 80 in water at a concentration of 0.4 mg/mL was served as the liquid stream 2. Water was served as each of the liquid streams 3, 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic drug-loaded liposomes. The mixing might last for an appropriate period of time depending on a desired volume of the suspension of cationic drug-loaded liposomes. In this example, the mixing lasted for 10 seconds. The resulting suspension of cationic drug-loaded liposomes had an aqueous phase and an organic phase in a volume ratio (v:v) of 1:3. In order to achieve a homogeneous suspension of cationic drug-loaded liposomes, the mixture formed in the first 2 seconds was discarded and the mixture formed in the subsequent 8 seconds was collected as the suspension of cationic drug-loaded liposomes. The collected suspension of cationic drug-loaded liposomes was dialyzed for 10 hours in a dialysis bag and the water was exchanged for fresh water at 2-hour intervals. Particle size and surface potential of the cationic drug-loaded liposomes were measured and characterized using a Malvern ZS90 instrument. The high-performance liquid chromatography (HPLC) system was used to measure a drug loading of the cationic drug-loaded liposomes, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 5 was obtained.

Example 6

1,2-dipalmitoyl-3-trimethylammonium-propane (DPTAP), DC-cholesterol and sirolimus were dissolved in ethanol to form a solution serving as the liquid stream 1 and having concentrations of 3 mg/mL of DPTAP, 1 mg/mL of DC-cholesterol and 8 mg/mL of sirolimus. A solution of poloxamer 188 in water at a concentration of 0.4 mg/mL was served as the liquid stream 2. Water was served as the liquid streams 3, 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic drug-loaded liposomes. The mixing might last for an appropriate period of time depending on a desired volume of the suspension of cationic drug-loaded liposomes. In this example, the mixing lasted for 10 seconds. The resulting suspension of cationic drug-loaded liposomes had an aqueous phase and an organic phase in a volume ratio (v:v) of 1:3. In order to achieve a homogeneous suspension of cationic drug-loaded liposomes, the mixture formed in the first 2 seconds was discarded and the mixture formed in the subsequent 8 seconds was collected as the suspension of cationic drug-loaded liposomes. The collected suspension of cationic drug-loaded liposomes was dialyzed for 10 hours in a dialysis bag and the water was exchanged for fresh water at 2-hour intervals. Particle size and surface potential of the cationic drug-loaded liposomes were measured and characterized using a Malvern ZS90 instrument. The high-performance liquid chromatography (HPLC) system was used to measure a drug loading of the cationic drug-loaded liposomes, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 6 was obtained.

Example 7

1,2-distearoyl-3-trimethylammonium-propane (DSTAP), DC-cholesterol, DOTAP and sirolimus were dissolved in ethanol to form a solution serving as the liquid stream 1 and having concentrations of 3 mg/mL of DSTAP, 1 mg/mL of DC-cholesterol, 1 mg/mL of DOTAP and 8 mg/mL of sirolimus. A pH 7 solution of carbomer 940 in water at a concentration of 0.4 mg/mL was served as the liquid stream 2. Water was served as the liquid streams 3, 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic drug-loaded liposomes. The mixing might last for an appropriate period of time depending on a desired volume of the suspension of cationic drug-loaded liposomes. In this example, the mixing lasted for 10 seconds. The resulting suspension of cationic drug-loaded liposomes had an aqueous phase and an organic phase in a volume ratio (v:v) of 1:3. In order to achieve a homogeneous suspension of cationic drug-loaded liposomes, the mixture formed in the first 2 seconds was discarded and the mixture formed in the subsequent 8 seconds was collected as the suspension of cationic drug-loaded liposomes. The collected suspension of cationic drug-loaded liposomes was dialyzed for 10 hours in a dialysis bag and the water was exchanged for fresh water at 2-hour intervals. Particle size and surface potential of the cationic drug-loaded liposomes were measured and characterized using a Malvern ZS90 instrument. The high-performance liquid chromatography (HPLC) system was used to measure a drug loading of the cationic drug-loaded liposomes, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 7 was obtained.

Example 8

Sirolimus, D-α-tocopherol polyethylene glycol succinate (TPGS) and poly(lactic-co-glycolic acid) (PLGA) were completely dissolved in acetone to form a solution serving as the liquid stream 1 and having concentrations of 10 mg/mL of sirolimus, 2 mg/mL of TPGS and 5 mg/mL of PLGA. TPGS and chitosan hydrochloride were dissolved in water to form the solution serving as the liquid stream 2 and having concentrations of 0.3 mg/mL of TPGS and 0.08 mg/mL of chitosan hydrochloride. Water was served as both the liquid stream 3 and liquid stream 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic nanodrug particles. The mixing might last for an appropriate period of time depending on a desired volume of the suspension of cationic nanodrug particles. In this example, the mixing lasted for 10 seconds, and the resulting suspension of cationic nanodrug particles had an aqueous phase and an organic phase in a volume ratio of 1:3. In order to achieve a homogeneous suspension, the mixture formed in the first 2 seconds was discarded and the mixture formed in the subsequent 8 seconds was collected as the suspension of cationic nanodrug particles. The collected suspension of cationic nanodrug particles was dialyzed for 12 hours in a dialysis bag and the water was exchanged for fresh water at 2-hour intervals. The so-processed suspension of nanodrug particles was then concentrated for subsequent use. Particle size and surface potential of the nanodrug particles were measured and characterized using a Malvern ZS90 instrument. The high-performance liquid chromatography (HPLC) system was used to measure a drug loading of the nanodrug particles, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 8 was obtained.

Example 9

Sirolimus, D-α-tocopherol polyethylene glycol succinate (TPGS) and poly(lactic-co-glycolic acid) (PLGA) were completely dissolved in acetone to form a solution serving as the liquid stream 1 and having concentrations of 10 mg/mL of sirolimus, 2 mg/mL of TPGS and 5 mg/mL of PLGA. TPGS and N,N,N-trimethyl chitosan (TMC) were dissolved in water to form the solution serving as the liquid stream 2 and having concentrations of 0.3 mg/mL of TPGS and 0.08 mg/mL of TMC. Water was served as both the liquid stream 3 and liquid stream 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic nanodrug particles. The mixing might last for an appropriate period of time depending on a desired volume of the suspension of cationic nanodrug particles. In this example, the mixing lasted for 10 seconds, and the resulting suspension of cationic nanodrug particles had an aqueous phase and an organic phase in a volume ratio of 1:3. In order to achieve a homogeneous suspension, the mixture formed in the first 2 seconds was discarded and the mixture formed in the subsequent 8 seconds was collected as the suspension of cationic nanodrug particles. The collected suspension of cationic nanodrug particles was dialyzed for 12 hours in a dialysis bag and the water was exchanged for fresh water at 2-hour intervals. The so-processed suspension of nanodrug particles was then concentrated for subsequent use. Particle size and surface potential of the nanodrug particles were measured and characterized using a Malvern ZS90 instrument. The high-performance liquid chromatography (HPLC) system was used to measure a drug loading of the nanodrug particles, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 9 was obtained.

Example 10

Sirolimus, D-α-tocopherol polyethylene glycol succinate (TPGS) and poly(lactic-co-glycolic acid) (PLGA) were completely dissolved in acetone to form a solution serving as the liquid stream 1 and having concentrations of 10 mg/mL of sirolimus, 2 mg/mL of TPGS and 5 mg/mL of PLGA. TPGS and diethylaminoethyl-dextran (DEAE-dextran) were dissolved in water to form the solution serving as the liquid stream 2 and having concentrations of 0.3 mg/mL of TPGS and 0.08 mg/mL of DEAE-dextran. Water was served as both the liquid stream 3 and liquid stream 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic nanodrug particles. The mixing might last for an appropriate period of time depending on a desired volume of the suspension of cationic nanodrug particles. In this example, the mixing lasted for 10 seconds, and the resulting suspension of cationic nanodrug particles had an aqueous phase and an organic phase in a volume ratio of 1:3. In order to achieve a homogeneous suspension, the mixture formed in the first 2 seconds was discarded and the mixture formed in the subsequent 8 seconds was collected as the suspension of cationic nanodrug particles. The collected suspension of cationic nanodrug particles was dialyzed for 12 hours in a dialysis bag and the water was exchanged for fresh water at 2-hour intervals. The so-processed suspension of nanodrug particles was then concentrated for subsequent use. Particle size and surface potential of the nanodrug particles were measured and characterized using a Malvern ZS90 instrument. The high-performance liquid chromatography (HPLC) system was used to measure a drug loading of the nanodrug particles, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 10 was obtained.

Example 11

Sirolimus, D-α-tocopherol polyethylene glycol succinate (TPGS) and poly(lactic-co-glycolic acid) (PLGA) were completely dissolved in acetone to form a solution serving as the liquid stream 1 and having concentrations of 10 mg/mL of sirolimus, 2 mg/mL of TPGS and 5 mg/mL of PLGA. TPGS and polyarginine (Peptide R9) were dissolved in water to form the solution serving as the liquid stream 2 and having concentrations of 0.3 mg/mL of TPGS and 0.08 mg/mL of Peptide R9. Water was served as both the liquid stream 3 and liquid stream 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic nanodrug particles. The mixing might last for an appropriate period of time depending on a desired volume of the suspension of cationic nanodrug particles. In this example, the mixing lasted for 10 seconds, and the resulting suspension of cationic nanodrug particles had an aqueous phase and an organic phase in a volume ratio of 1:3. In order to achieve a homogeneous suspension, the mixture formed in the first 2 seconds was discarded and the mixture formed in the subsequent 8 seconds was collected as the suspension of cationic nanodrug particles. The collected suspension of cationic nanodrug particles was dialyzed for 12 hours in a dialysis bag and the water was exchanged for fresh water at 2-hour intervals. The so-processed suspension of nanodrug particles was then concentrated for subsequent use. Particle size and surface potential of the nanodrug particles were measured and characterized using a Malvern ZS90 instrument. The high-performance liquid chromatography (HPLC) system was used to measure a drug loading of the nanodrug particles, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 11 was obtained.

Example 12

Distearoyl phosphoethanolamine (DSPE), DC-cholesterol, DOTAP and sirolimus were dissolved in ethanol to form a solution serving as the liquid stream 1 and having concentrations of 3 mg/mL of DPTAP, 1 mg/mL of DC-cholesterol, 1 mg/mL of DOTAP and 8 mg/mL of sirolimus. A solution of TPGS in water at a concentration of 0.4 mg/mL was served as the liquid stream 2. Water was served as the liquid streams 3, 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic drug-loaded liposomes. The mixing might last for an appropriate period of time depending on a desired volume of the suspension of cationic drug-loaded liposomes. In this example, the mixing lasted for 10 seconds. The resulting suspension of cationic drug-loaded liposomes had an aqueous phase and an organic phase in a volume ratio (v:v) of 1:3. In order to achieve a homogeneous suspension of cationic drug-loaded liposomes, the mixture formed in the first 2 seconds was discarded and the mixture formed in the subsequent 8 seconds was collected as the suspension of cationic drug-loaded liposomes. The collected suspension of cationic drug-loaded liposomes was dialyzed for 10 hours in a dialysis bag and the water was exchanged for fresh water at 2-hour intervals. Particle size and surface potential of the cationic drug-loaded liposomes were measured and characterized using a Malvern ZS90 instrument. The high-performance liquid chromatography (HPLC) system was used to measure a drug loading of the cationic drug-loaded liposomes, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 12 was obtained.

Example 13

1,2-dioleoyl-sn-glycero-3-phosphoethanolamine (DOPE), DC-cholesterol, DOTAP and sirolimus were dissolved in ethanol to form a solution having concentrations of 3 mg/mL of DOPE, 1 mg/mL of DC-cholesterol, 1 mg/mL of DOTAP and 8 mg/mL of sirolimus. A suspension of cationic drug-loaded liposomes was then obtained by dropwise adding 1 mL of the above solution slowly to stirred water and stirring the aqueous solution (10 mL) overnight. Therefore, the resulting suspension of cationic drug-loaded liposomes had an aqueous phase and an organic phase in a volume ratio of 1:10. The above suspension of cationic drug-loaded liposomes was dialyzed for 10 hours in a dialysis bag and the water was exchanged for fresh water at 2-hour intervals. Particle size and surface potential of the cationic drug-loaded liposomes were measured and characterized using a Malvern ZS90 instrument. The high-performance liquid chromatography (HPLC) system was used to measure a drug loading of the cationic drug-loaded liposomes, and a transmission electron microscope (TEM) was used to observe the morphology of the particles.

Example 14

1,2-dioleoyl-sn-glycero-3-phosphoethanolamine (DOPE), DC-cholesterol and DOTAP were dissolved in ethanol to form a solution serving as the liquid stream 1 and having concentrations of 3 mg/mL of DOPE, 1 mg/mL of DC-cholesterol, and 1 mg/mL of DOTAP. A solution of TPGS in water at a concentration of 0.4 mg/mL was served as the liquid stream 2. Water was served as the liquid streams 3, 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic drug-loaded liposomes. The mixing might last for an appropriate period of time depending on a desired volume of the suspension of cationic drug-loaded liposomes. In this example, the mixing lasted for 10 seconds. The resulting suspension of cationic drug-loaded liposomes had an aqueous phase and an organic phase in a volume ratio (v:v) of 1:3. In order to achieve a homogeneous suspension of cationic drug-loaded liposomes, the mixture formed in the first 2 seconds was discarded and the mixture formed in the subsequent 8 seconds was collected as the suspension of cationic drug-loaded liposomes. The collected suspension of cationic drug-loaded liposomes was dialyzed for 10 hours in a dialysis bag and the water was exchanged for fresh water at 2-hour intervals. Particle size and surface potential of the cationic drug-loaded liposomes were measured and characterized using a Malvern ZS90 instrument. The high-performance liquid chromatography (HPLC) system was used to measure a drug loading of the cationic drug-loaded liposomes.

Example 15

A two-channel mixer was used to prepare a cationic nanodrug.

Sirolimus, poloxamer 407 and poly(lactic-co-glycolic acid) (PLGA) were dissolved in acetone to form a solution serving as the liquid stream 1 and having concentrations of 10 mg/mL of sirolimus, 2 mg/mL of poloxamer 407, and 5 mg/mL of PLGA. A solution of TPGS and hydroxypropyltrimethyl ammonium chloride chitosan (HACC) in water at a concentration of 0.3 mg/mL and 0.08 mg/mL, respectively, was served as the liquid stream 2. These liquids were then introduced by an injection pump to a two-channel vortex mixer as two liquid streams (i.e., said liquid streams 1 and 2) at a flow rate of 10 mL/min, where they were mixed to form a suspension of cationic drug-loaded particles. The mixing might last for an appropriate period of time depending on a desired volume of the suspension of cationic drug-loaded particles. In this example, the mixing lasted for 10 seconds. The resulting suspension of cationic drug-loaded particles had an aqueous phase and an organic phase in a volume ratio (v:v) of 1:1. In order to achieve a homogeneous suspension of cationic drug-loaded particles, the mixture formed in the first 2 seconds was discarded and the mixture formed in the subsequent 8 seconds was collected as the suspension of cationic drug-loaded particles. The collected suspension of cationic drug-loaded particles was dialyzed for 12 hours in a dialysis bag and the water was exchanged for fresh water at 2-hour intervals. Particle size and surface potential of the cationic drug-loaded particles were measured and characterized using a Malvern ZS90 instrument. The high-performance liquid chromatography (HPLC) system was used to measure a drug loading of the cationic drug-loaded particles, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 15 was obtained.

Example 16

Example 16 differs from Example 1 in the flow rate ratio of either of the first and second liquid streams to either of the third and fourth liquid streams.

Sirolimus, D-α-tocopherol polyethylene glycol succinate (TPGS) and poly(lactic-co-glycolic acid) (PLGA) were completely dissolved in acetone to form a solution serving as the liquid stream 1 and having concentrations of 10 mg/mL of sirolimus, 2 mg/mL of TPGS and 5 mg/mL of PLGA. TPGS and hydroxypropyltrimethyl ammonium chloride chitosan (HACC) were dissolved in water to form the solution serving as the liquid stream 2 and having concentrations of 0.3 mg/mL of TPGS and 0.08 mg/mL of HACC. Water was served as both the liquid stream 3 and liquid stream 4. These liquids were then introduced by an injection pump to a four-channel vortex mixer as four liquid streams (i.e., said liquid streams 1, 2, 3 and 4) where they were mixed to form a suspension of cationic nanodrug particles. Either of liquid stream 1 and liquid stream 2 was introduced at a flow rate of 10 mL/min, and either of liquid stream 3 and liquid stream 4 was introduced at a flow rate of 40 mL/min. The mixing might last for an appropriate period of time depending on a desired volume of the suspension of cationic nanodrug particles. In this example, the mixing lasted for 10 seconds, and the resulting suspension of cationic nanodrug particles had an aqueous phase and an organic phase in a volume ratio of 1:9. In order to achieve a homogeneous suspension, the mixture formed in the first 2 seconds was discarded and the mixture formed in the subsequent 8 seconds was collected as the suspension of cationic nanodrug particles. The collected suspension of cationic nanodrug particles was dialyzed for 12 hours in a dialysis bag and the water was exchanged for fresh water at 2-hour intervals. The so-processed suspension of nanodrug particles was then concentrated for subsequent use. Particle size and surface potential of the nanodrug particles were measured and characterized using a Malvern ZS90 instrument. The high-performance liquid chromatography (HPLC) system was used to measure a drug loading of the nanodrug particles, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 16 was obtained.

Comparative Example 1

This example was substantially the same as Example 1 except that no cationic modifier was added to the second liquid stream.

Sirolimus, D-α-tocopherol polyethylene glycol succinate (TPGS) and poly(lactic-co-glycolic acid) (PLGA) were completely dissolved in acetone to form a solution serving as the liquid stream 1 and having concentrations of 10 mg/mL of sirolimus, 2 mg/mL of TPGS and 5 mg/mL of PLGA. TPGS was dissolved in water to form the solution serving as the liquid stream 2 and having a concentration of 0.3 mg/mL of TPGS. Water was served as both the liquid stream 3 and liquid stream 4. These liquids were then introduced by an injection pump to a four-channel vortex mixer as four liquid streams (i.e., said liquid streams 1, 2, 3 and 4) at a flow rate of 10 mL/min, where they were mixed to form a suspension of nanodrug particles. The mixing might last for an appropriate period of time depending on a desired volume of the suspension of cationic nanodrug particles. In this example, the mixing lasted for 10 seconds, and the resulting suspension of nanodrug particles had an aqueous phase and an organic phase in a volume ratio of 1:3. In order to achieve a homogeneous suspension, the mixture formed in the first 2 seconds was discarded and the mixture formed in the subsequent 8 seconds was collected as the suspension of cationic nanodrug particles. The collected suspension of nanodrug particles was dialyzed for 12 hours in a dialysis bag and the water was exchanged for fresh water at 2-hour intervals. The so-processed suspension of cationic nanodrug particles was then concentrated for subsequent use. Particle size and surface potential of the nanodrug particles were measured and characterized using a Malvern ZS90 instrument. The high-performance liquid chromatography (HPLC) system was used to measure a drug loading of the nanodrug particles, and a transmission electron microscope (TEM) was used to observe the morphology of the particles.

The balloon having a hydrophilic coating is provided. The prepared cationic nanodrug particles above were ultrasonically sprayed uniformly on the surface of the balloon until a concentration of the drug reached 1.3 mg/mm$^2$. Then, the balloon was naturally dried for 24 hours and sterilization by epoxyethane. In this way, a drug-coated balloon of Example 1 was obtained.

Comparative Example 2

This example was substantially the same as Example 1 except that no drug was load on the cationic nanoparticle.

D-α-tocopherol polyethylene glycol succinate (TPGS) and poly(lactic-co-glycolic acid) (PLGA) were completely dissolved in acetone to form a solution serving as the liquid stream 1 and having concentrations of 2 mg/mL of TPGS and 5 mg/mL of PLGA. TPGS and hydroxypropyltrimethyl ammonium chloride chitosan (HACC) was dissolved in water to form the solution serving as the liquid stream 2 and having concentrations of 0.3 mg/mL of TPGS and 0.08 mg/mL of HACC. Water was served as both the liquid stream 3 and liquid stream 4. These liquids were then introduced by an injection pump to a four-channel vortex mixer as four liquid streams (i.e., said liquid streams 1, 2, 3 and 4) at a flow rate of 10 mL/min, where they were mixed to form a suspension of nanodrug particles. The mixing might last for an appropriate period of time depending on a desired volume of the suspension of cationic nanodrug particles. In this example, the mixing lasted for 10 seconds, and the resulting suspension of nanodrug particles had an aqueous phase and an organic phase in a volume ratio of 1:3. In order to achieve a homogeneous suspension, the mixture formed in the first 2 seconds was discarded and the mixture formed in the subsequent 8 seconds was collected as the suspension of cationic nanodrug particles. The collected suspension of nanodrug particles was dialyzed for 12 hours in a dialysis bag and the water was exchanged for fresh water at 2-hour intervals. The so-processed suspension of cationic nanodrug particles was then concentrated for subsequent use. Particle size and surface potential of the nanodrug particles were measured and characterized using a Malvern ZS90 instrument.

Comparative Example 3

This example was substantially the same as comparative Example 2 (i.e., no drug was loaded) except that the didodecyldimethylammonium bromide (DMAB) was used in place of the cationic modifier hydroxypropyltrimethyl ammonium chloride chitosan (HACC).

D-α-tocopherol polyethylene glycol succinate (TPGS) and poly(lactic-co-glycolic acid) (PLGA) were completely dissolved in acetone to form a solution serving as the liquid stream 1 and having concentrations of 2 mg/mL of TPGS and 5 mg/mL of PLGA. TPGS and didodecyldimethylammonium bromide (DMAB) was dissolved in water to form the solution serving as the liquid stream 2 and having concentrations of 0.3 mg/mL of TPGS and 0.08 mg/mL of DMAB. Water was served as both the liquid stream 3 and liquid stream 4. These liquids were then introduced by an injection pump to a four-channel vortex mixer as four liquid streams (i.e., said liquid streams 1, 2, 3 and 4) at a flow rate of 10 mL/min, where they were mixed to form a suspension of nanodrug particles. The mixing might last for an appropriate period of time depending on a desired volume of the suspension of cationic nanodrug particles. In this example, the mixing lasted for 10 seconds, and the resulting suspension of nanodrug particles had an aqueous phase and an organic phase in a volume ratio of 1:3. In order to achieve a homogeneous suspension, the mixture formed in the first 2 seconds was discarded and the mixture formed in the subsequent 8 seconds was collected as the suspension of cationic nanodrug particles. The collected suspension of nanodrug particles was dialyzed for 12 hours in a dialysis bag and the water was exchanged for fresh water at 2-hour intervals. The so-processed suspension of cationic nanodrug particles was then concentrated for subsequent use. Particle size and surface potential of the nanodrug particles were measured and characterized using a Malvern ZS90 instrument.

Comparative Example 4

1,2-dioleoyl-3-trimethylammonium-propane chloride (DOTAP) and DC-cholesterol were dissolved in ethanol to form a solution serving as the liquid stream 1 and having concentrations of 3 mg/mL of DOTAP and 1 mg/mL of DC-cholesterol. Water was served as the liquid streams 2, 3, 4. These liquids were then introduced by an injection pump to a four-channel vortex mixer as four liquid streams (i.e., said liquid streams 1, 2, 3 and 4) at a flow rate of 10 mL/min, where they were mixed to form a suspension of cationic drug-loaded liposomes. The mixing might last for an appropriate period of time depending on a desired volume of the suspension of cationic drug-loaded liposomes. In this example, the mixing lasted for 10 seconds. The resulting suspension of cationic drug-loaded liposomes had an aqueous phase and an organic phase in a volume ratio (v:v) of 1:3. In order to achieve a homogeneous suspension of cationic drug-loaded liposomes, the mixture formed in the first 2 seconds was discarded and the mixture formed in the subsequent 8 seconds was collected as the suspension of cationic drug-loaded liposomes. The collected suspension of cationic drug-loaded liposomes was dialyzed for 10 hours in a dialysis bag and the water was exchanged for fresh water at 2-hour intervals. Particle size and surface potential of the cationic drug-loaded liposomes were measured and characterized using a Malvern ZS90 instrument.

Performance Verification Tests (1) Particle Size, Surface Potential and Drug Loading Particle size and surface potential of the nanodrug particles of Examples 1-13 and Comparative Example 1 were tested and characterized using a Malvern ZS90 instrument (at a scattering angle of 90° and a temperature of 25° C.). Moreover, a high-performance liquid chromatography (HPLC) system (C18 column; mobile phase:acetonitrile: water:methanol=16%: 24%: 60%; flow rate: 1.0 mL/min; temperature: 40° C.; detector: UV 277 nm) was used to measure the drug loading of the nanodrug particle. The results are summarized in Table 1 below.

TABLE 1

| | Particle Size (nm) | Surface Potential (mV) | Drug Loading (%, w/w) |
|---|---|---|---|
| Example 1 | 249.7 ± 5.6 nm | 54.5 ± 1.3 mV | 41% |
| Example 2 | 192 ± 2.7 nm | 46.1 ± 2.5 mV | 40% |
| Example 3 | 250.2 ± 3.4 nm | 45.2 ± 0.6 mV | 40% |
| Example 4 | 330.1 ± 0.9 nm | 40.4 ± 1.1 mV | 48% |
| Example 5 | 352.4 ± 1.7 nm | 32.1 ± 1.2 mV | 46% |
| Example 6 | 290.5 ± 2.5 nm | 55.2 ± 4.1 mV | 37% |
| Example 7 | 362.1 ± 5.4 nm | 36.2 ± 0.7 mV | 33% |
| Example 8 | 195.2 ± 1.0 nm | 44.2 ± 1.6 mV | 46% |
| Example 9 | 206.4 ± 2.1 nm | 48.1 ± 1.8 mV | 45% |
| Example 10 | 240.3 ± 0.8 nm | 29.6 ± 0.9 mV | 42% |
| Example 11 | 232.2 ± 2.3 nm | 46.2 ± 2.2 mV | 43% |
| Example 12 | 280.3 ± 3.8 nm | 40.1 ± 3.1 mV | 39% |
| Example 13 | 451.2 ± 8.4 nm | 51.3 ± 2.8 mV | 22% |
| Example 15 | 538.1 ± 13.9 nm | 43.3 ± 6.8 mV | 37% |
| Example 16 | 213.4 ± 6.2 nm | 49.3 ± 5.5 mV | 35% |
| Comparative Example 1 | 195.8 ± 4.5 nm | −14.2 ± 0.9 mV | 41% |
| Comparative Example 3 | 195.8 ± 4.5 nm | −14.2 ± 0.9 mV | — |

Figure 2:
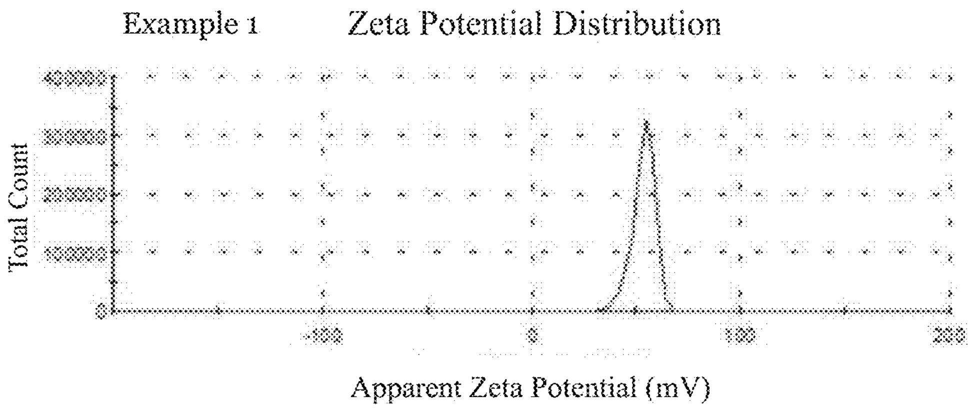
FIG. 2 shows the surface zeta potential distributions of Example 1 and Comparative Example 1.
Figure 2:
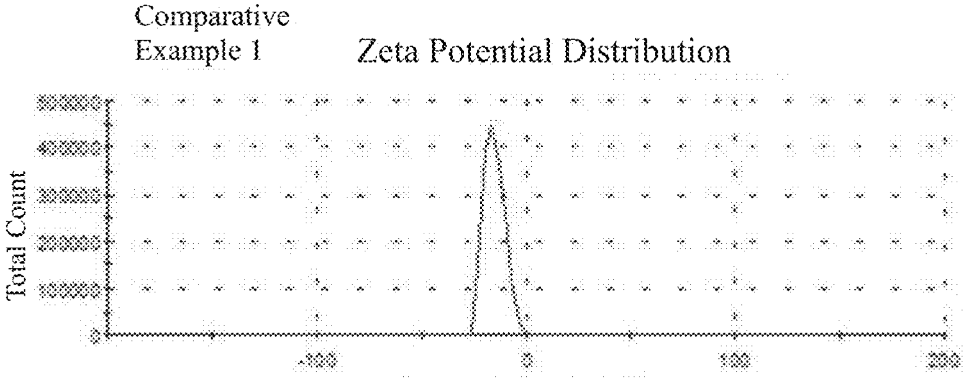

As can be seen from Table 1, the surface of the cationic nanodrugs from Examples 1-16 has positive charges, while the surface of the cationic nanodrugs from Comparative Example 1 has negative charges. FIG. 2 shows surface zeta potential distributions of Example 1 and Comparative Example 1. As apparently seen from FIG. 2, the nanodrug of Example 1 has positive charges at the surface and that of Comparative Example 1 has negative charges. This demonstrates that the addition of the cationic amphiphilic compound and/or cationic modifier enables the surface of the nanodrug particles to have positive charges.

In addition, Examples 1 and 16 are substantially the same except that both the third and fourth liquid streams in Example 16 have an increased flow rate. The finer particle size of the nanoparticles prepared in Example 16 demonstrates that the instantaneous nanoprecipitation process is effective in adjusting particle size of nanoparticles.

Figure 3:
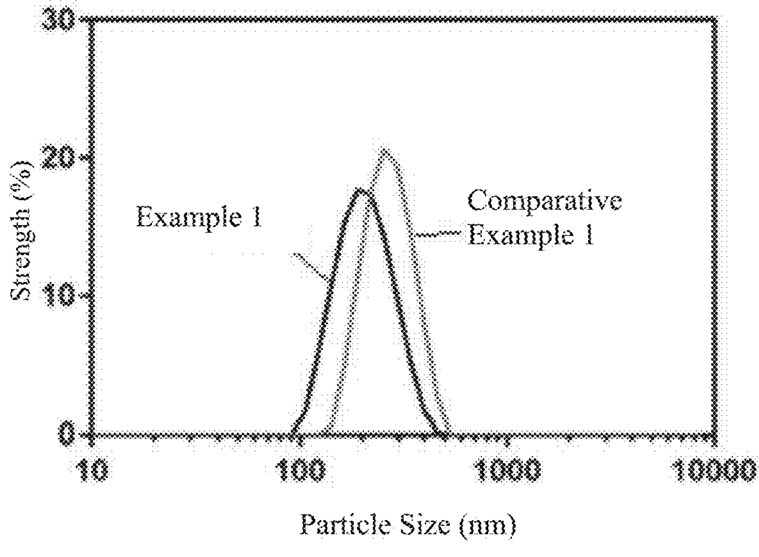
FIG. 3 shows particle size distributions of cationic nanodrug particles of Example 1 and Comparative Example 1.
Figure 4:
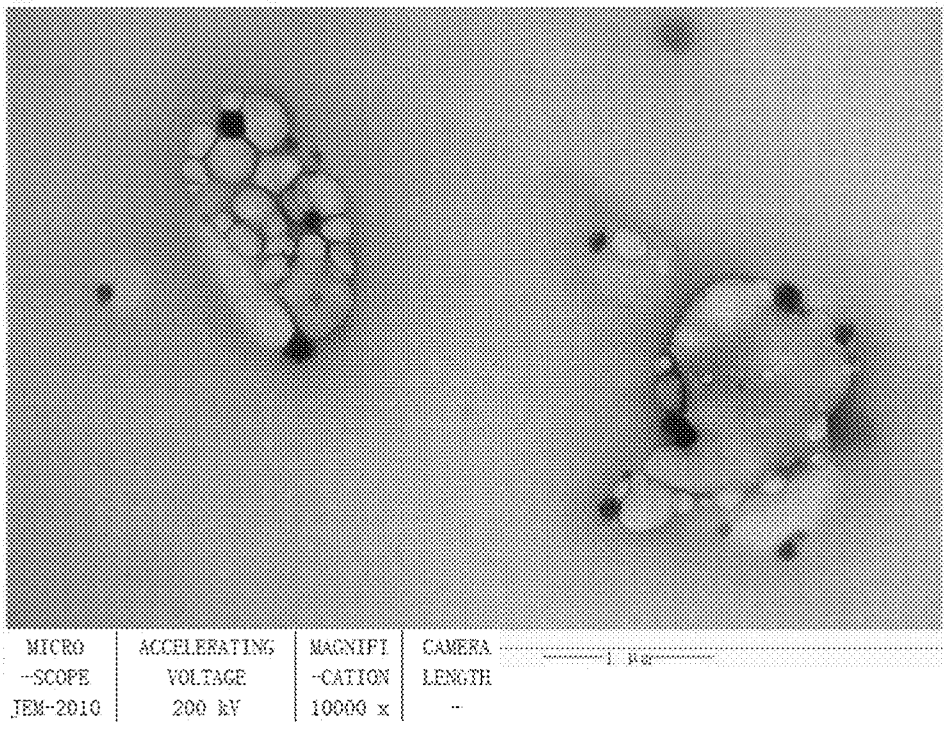
FIG. 4 shows the morphology of the cationic nanodrug of Example 1.
Figure 5:
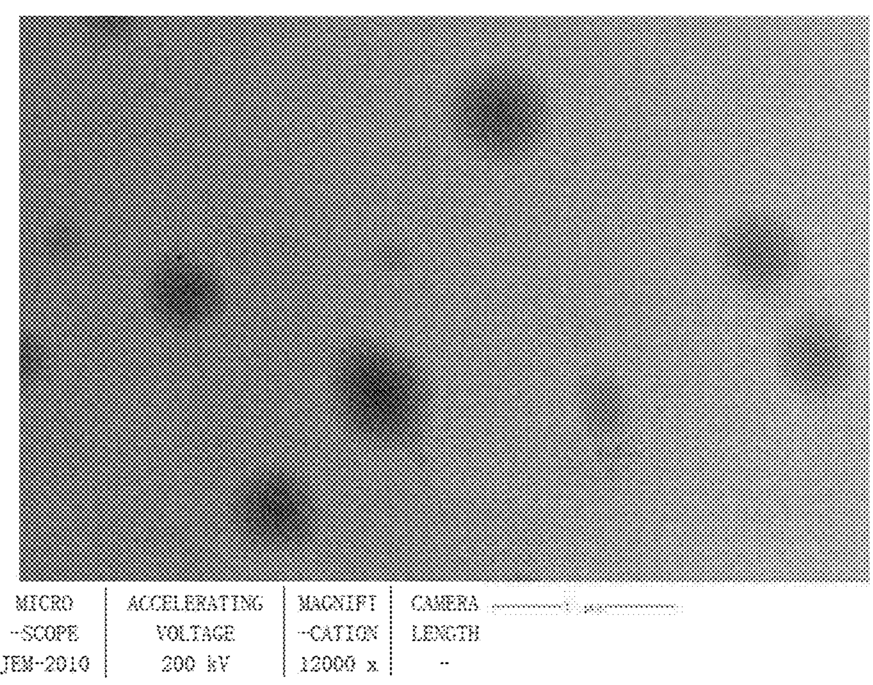
FIG. 5 shows the morphology of the cationic nanodrug of Example 13.

FIG. 3 shows particle size distributions of the cationic nanodrug particles of Examples 1 and 13, which are prepared respectively by instantaneous nanoprecipitation and a conventional stirring method. As can be seen from FIG. 1, Example 1 achieves a smaller particle size than Example 13. FIG. 4 shows the morphology of the cationic nanodrug of Example 1, and FIG. 5 shows the morphology of the nanodrug of Example 13. As can be seen, the morphology of the cationic nanodrug particles prepared by instantaneous nanoprecipitation is better.

Examples 13 and 2 are substantially the same except that the drugs are prepared by different methods. As can be seen from Table 1, the drug loading of Example 2 is significantly greater than that of Example 13, demonstrating that instantaneous nanoprecipitation enables to significantly increase the drug loading of the prepared cationic nanodrug.

(2) Tissue Uptake Test

Swine arterial blood vessel segments were harvested and maintained at a constant temperature of 37° C. Each segment was expanded by a sterilized bare balloon at 6 atm for 1 min and then the balloon was deflated and removed. Subsequently, each of the drug-loaded balloons prepared in Examples 1-12 and Comparative Example 1 was placed into one of the expanded blood vessel segments, inflated at 6 atm for 1 min, deflated and removed. The blood vessel segment was immediately washed with a phosphate buffered saline (PBS) solution (3 times, 1 mL each time) and then tissue drug concentration was determined by gas chromatography-mass spectrometry (GC-MS). The results are summarized in Table 2 below.

TABLE 2

| | Tissue Drug Concentration (ng/mg) |
|---|---|
| Example 1 | 404.8 ± 157.9 |
| Example 2 | 507.5 ± 230.3 |
| Example 3 | 483.7 ± 217.5 |
| Example 4 | 303.4 ± 110.5 |
| Example 5 | 324.9 ± 122.3 |
| Example 6 | 284.2 ± 140.1 |
| Example 7 | 349.2 ± 110.3 |
| Example 8 | 286.7 ± 87.6 |
| Example 9 | 372.5 ± 176.6 |
| Example 10 | 384.8 ± 88.7 |
| Example 11 | 389.7 ± 154.2 |
| Example 12 | 325.2 ± 91.3 |
| Example 13 | 385.5 ± 103.3 |
| Comparative Example 1 | 131.8 ± 41.6 |

As can be seen from Table 2, the cationic nanodrugs of Examples 1-13 all exhibit superior tissue uptake properties, which are significantly improved over that of Comparative Example 1. This demonstrates that the positively charged nanodrugs is more favorable to the tissue uptake.

(3) Tissue Retention Time

Swine arterial blood vessel segments were harvested and maintained at a constant temperature of 37° C. Each segment was expanded by a sterilized bare balloon at 6 atm for 1 min and then the balloon was deflated and removed. Subsequently, each of the drug-loaded balloons prepared in Examples 1-12 and Comparative Example 1 was placed into one of the expanded blood vessel segments, inflated at 6 atm for 1 min, deflated and removed. The blood vessel segment was immediately washed with a phosphate buffered saline (PBS) solution (3 times, 1 mL each time).

The swine arterial blood vessel segments that had been implanted with the drug-loaded balloons were cultivated in culture media, and samples were taken at day 7, day 14 and day 28 for each of the segments. Three duplicate samples were taken at each sampling time. The tissue drug concentration for these samples were determined by gas chromatography-mass spectrometry (GC-MS). The results are summarized in Table 3 below.

TABLE 3

| | Tissue Drug Concentration (ng/mg) | | |
|---|---|---|---|
| | Day 7 | Day 14 | Day 28 |
| Example 1 | 92.4 ± 13.9 | 24.8 ± 5.9 | 10 ± 5.7 |
| Example 2 | 82.8 ± 18.2 | 16.2 ± 9.3 | 9.2 ± 3.4 |
| Example 3 | 62.8 ± 19.1 | 18.1 ± 7.2 | 1.9 ± 1.1 |
| Example 4 | 54.1 ± 22.1 | 20.5 ± 1.1 | 3.8 ± 1.9 |
| Example 5 | 67.9 ± 12.5 | 16.1 ± 8.6 | 2.1 ± 5.5 |
| Example 6 | 59.3 ± 21.4 | 16 ± 7.3 | 3.9 ± 3.6 |
| Example 7 | 61.6 ± 22.8 | 14.8 ± 7.4 | 0.7 ± 0.3 |
| Example 8 | 58.6 ± 17 | 14 ± 8.1 | 2.6 ± 0.7 |
| Example 9 | 69.7 ± 22.4 | 19.8 ± 8.9 | 1.3 ± 0.3 |
| Example 10 | 49.9 ± 18.5 | 14.2 ± 7.1 | 8.6 ± 3.4 |
| Example 11 | 42.1 ± 14 | 10.6 ± 13.1 | 0.3 ± 1.3 |
| Example 12 | 58 ± 20.5 | 12.8 ± 7.6 | 1.1 ± 2.2 |
| Example 13 | 31.2 ± 11.7 | 4.3 ± 3.1 | BQL |
| Comparative Example 1 | 7.6 ± 0.6 | BQL | BQL |

BQL: Below Quantification Limit

As can be seen from Table 3, the cationic nanodrugs of Examples 1-13 all exhibit superior sustained release properties, and are able to prolong the release time of the drug. In contrast, the nanodrug of Comparative Example 1 almost has no sustained release effect. A comparison drawn between Examples 2 and 13 reveals a significantly improved sustained release effect of Example 2 over Example 13.

(4) Cytotoxicity of the Cationic Substances

Vascular smooth muscle cells (SMCs) were collected and the cell concentration was determined using a hemocytometer. The cell concentration was adjusted to 105 per mL using a liquid cell culture medium. The cell suspension was dispensed on a 96-well plate (104 cells in each well) and the wells were divided into groups (a control group and four test groups), four wells for each group. After the cells were cultivated for 24 hours under regular cell culture conditions, the culture medium was pipetted away. Each of the fresh culture media and culture media respectively containing the suspensions of non-drug loaded nanoparticles prepared in Example 14, Comparative Example 2 and Comparative Example 3 was added (the cationic substance in each of the three examples has a same concentration). After the cells were further cultivated for 24 hours, 50 μL of an MTT agent was dispensed into each well, and the cells were then incubated for 4 hours in a $CO_2$ incubator. After that, the culture media were carefully pipetted away, and 150 μL of dimethyl sulfoxide was added to each well. The plate was then shaken gently to facilitate dissolution of formazan. Absorbance of each well at 490 nm was measured using a microplate reader, and cell survival rates were calculated according to:

$$\text{Survival Rate }\% = \frac{\text{Absorbance of Test Group}}{\text{Absorbance of Control Group}}$$

The results are summarized in Table 4 below.

TABLE 4

| | Cell Survival Rate % |
|---|---|
| Control | 100 |
| Example 14 | 97 |
| Comparative Example 2 | 91 |
| Comparative Example 3 | 68 |
| Comparative Example 4 | 96 |

As can be seen from Table 4, the cationic nanodrug of Example 14 exhibits almost no cytotoxicity and a high cell viability. In contrast, DMAB used in Comparative Example 3 shows serious cytotoxicity and is not suitable for use in drug loading. Further, the cationic amphiphilic compound DOTAP used in Comparative Example 4 has good biocompatibility and does not show noticeable cytotoxicity.

The various technical features of the foregoing embodiments may be combined in any way. Although not all such combinations have been described above for the sake of brevity, any of them is considered to fall within the scope of this specification as long as there is no contradiction between the technical features.

Presented above are merely several embodiments of the present application. Although these embodiments are described with some particularity and in some detail, it should not be construed that they limit the scope of the present application in any sense. Note that various variations and modifications can be made by those of ordinary skill in the art without departing from the concept of the present application. Accordingly, it is intended that all such variations and modifications are embraced within the scope of this application as defined in the appended claims.

What is claimed is:

1. A method of preparing a cationic nanodrug, comprising the steps of:

providing a first liquid stream;

providing a second liquid stream; and performing an instantaneous nanoprecipitation process in which the first and second liquid streams collide with each other to create a vortex stream where the two streams are mixed to form a nanosuspension, and obtaining the cationic nanodrug through collecting and dialyzing the nanosuspension, wherein a drug is dissolved in at least one of the first and second liquid streams and a a carrier is dissolved in the other one of the first and second liquid streams, wherein the drug is an antiproliferative drug selected from one or more of the group consisting of paclitaxel, sirolimus and derivatives of sirolimus, wherein one of the first and second liquid streams contains a water-soluble organic phase, and the other one of the first and second liquid streams contains an aqueous phase, wherein the carrier comprises one or more of a cationic amphiphilic compound and a cationic modifier, the cationic amphiphilic compound being an amino- and/or acyl-containing cationic amphiphilic compound, the cationic modifier being an amino- and/or acyl-containing cationic modifier; wherein the cationic nanodrug has a particle size ranging from 50 nm to 250 nm; wherein the particle size is uniform; wherein a surface potential of the cationic nanodrug is adjusted by changing contents of the cationic amphiphilic compound and the cationic modifier, and wherein the cationic nanodrug has a surface charge of 10-60 mV.

2. The method of claim 1, wherein a sustained release copolymer is dissolved in at least one of the first and second liquid streams, and/or an emulsifier is dissolved in at least one of the first and second liquid streams.

3. The method of claim 2, wherein the sustained release copolymer is poly(lactic-co-glycolic acid), and the emulsifier is selected from one or more of the group consisting of D-α-tocopherol polyethylene glycol succinate, polyvinyl alcohol, polysorbate, poloxamer and carbomer.

4. The method of any of claim 1, wherein performing the instantaneous nanoprecipitation process in which the first and second liquid streams collide with each other to create the vortex stream comprises the steps of:

providing a vortex mixer;

introducing the first liquid stream into one channel of the vortex mixer;

introducing the second liquid stream to another channel of the vortex mixer; and colliding and mixing the first liquid stream with the second liquid stream in the vortex mixer to form the vortex stream.

5. The method of claim 4, wherein performing the instantaneous nanoprecipitation process in which the first and second liquid streams collide with each other to create the vortex stream further comprises introducing water into remaining channel(s) of the vortex mixer as additional liquid stream(s); and colliding and mixing the first liquid stream, the second liquid stream and the additional liquid stream(s) in the vortex mixer to form the vortex stream.

6. The method of claim 5, wherein the additional liquid stream(s) comprise(s) a third liquid stream and a fourth liquid stream.

7. The method of claim 6, wherein the third and the fourth liquid streams have the same flow rate.

8. The method of claim 6, wherein each of the first, second and third liquid streams is introduced at a flow rate in the range of 1 mL/min to 12 mL/min, wherein a ratio of a flow rate of the first liquid stream to a flow rate of the second liquid stream is 1:1, and wherein the or each additional liquid stream in the remaining channel(s) is introduced at a flow rate that is 1 to 5 times that of the first or second liquid stream.

* * * * *